United States Patent
Tsai et al.

(10) Patent No.: US 8,053,474 B2
(45) Date of Patent: Nov. 8, 2011

(54) COMPOUND WITH CARBOXYL ACID GROUP AND AMIDE GROUP AND APPLICATION THEREOF

(75) Inventors: Wei-Chuan Tsai, Chiayi (TW); Chen-Yin Chen, Taichung (TW); Ming-Yi Chiu, Taipei (TW); Yi-Fan Ling, Yuanlin Township, Changhua County (TW); Nai-Hsuan Hsu, Jhonge (TW)

(73) Assignee: Corum Inc., Taipei (TW)

( * ) Notice: Subject to any disclaimer, the term of this patent is extended or adjusted under 35 U.S.C. 154(b) by 157 days.

(21) Appl. No.: 12/648,626

(22) Filed: Dec. 29, 2009

(65) Prior Publication Data

US 2011/0065954 A1 Mar. 17, 2011

(30) Foreign Application Priority Data

Sep. 11, 2009 (TW) .............................. 98130652 A

(51) Int. Cl.
*C07C 229/00* (2006.01)
*A61K 31/195* (2006.01)

(52) U.S. Cl. ........................................ 514/563; 562/565

(58) Field of Classification Search ........................ None
See application file for complete search history.

(56) References Cited

U.S. PATENT DOCUMENTS 2,653,898 A * 9/1953 Castillo et al. ................ 514/408

* cited by examiner

*Primary Examiner* — Paul A Zucker

(74) *Attorney, Agent, or Firm* — WPAT, PC; Justin King

(57) ABSTRACT

The present invention discloses compounds with a carboxyl acid group and an amide group which also containing the tertiary amino groups. The carboxyl acid group having a partial negative charge can attract the tertiary amino group with each other to form a quaternary ammonium salt structure, so that the compounds are easy to dissolve in water. Moreover, these compounds having a mushroom tyrosinase-inhibition effect and have the potential to use in the cosmetics for skin whitening.

19 Claims, 1 Drawing Sheet

COMPOUND WITH CARBOXYL ACID GROUP AND AMIDE GROUP AND APPLICATION THEREOF

BACKGROUND OF THE INVENTION

1. Field of the Invention

The present invention is generally related to a compound with a carboxyl acid group and an amide group, and more particularly to a water-soluble compound with a carboxyl acid group and an amide group.

2. Description of the Prior Art

Recently, compounds with carboxyl acid group(s) having skin whitening effect are often applied in cosmetic products. For example, azelaic acid is a common cosmetic raw material and has anti-acne and whitening effect. However, it has poor solubility to cosmetic base materials and this affects skin penetration and thereby results in formulation difficulties.

In order to develop better cosmetic materials, the skin whitening effect and the solubility to cosmetic base materials should be considered simultaneously. Thus, many compounds with carboxyl acid group(s) are synthesized successively. However, their water solubility is still not satisfied while generally commercial whitening products are aqueous solutions. For example, it is not easy to use non-salt solid compound with carboxyl acid group(s) together with an aqueous solution. Therefore, non-salt solid materials have limited application fields and lack of convenience.

In order to resolve such a problem, solid salts become very important in development. For example, the patent WO2006/010590A1 disclosed a compound with carboxyl acid salts, comprising a structure of alpha-amino acid and non-toxic cation, where its water solubility is from ion dissociation. That is, while in use, solid raw materials should dissolve in solvent and then be blended with other cosmetic raw materials. Thus, solid raw materials can not be blended with other materials directly to thereby result in inconvenience.

At present, compounds with carboxyl acid group(s) are still under development since their water solubility is still not satisfied. In view of the above description, a novel water-soluble compound with carboxyl acid group(s) is urgently needed.

SUMMARY OF THE INVENTION

In light of the above background, in order to fulfill the industrial requirements, the invention provides a novel compound with a carboxyl acid group and an amide group.

The present invention discloses a compound with a carboxyl acid group and an amide group that is solid. The compound with a carboxyl acid group and an amide group has the following general equation:

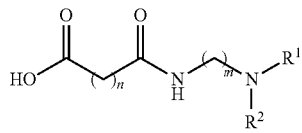

wherein n and m are both integers, n is 6~10, m is 2~4; $R^1$ and $R^2$ are the same, $R^1$ and $R^2$ are C1~C6 alkyl groups where the C1~C6 alkyl groups comprise C1~C6 linear alkyl groups and C1~C6 branched alkyl groups; the carboxyl acid group with a partial negative charge ($\delta-$) attracts the tertiary amino group to form a quaternary ammonium salt structure so that the compound is easily dissolved in water; and the carboxyl acid group and the amide group attracting to each other is shown in the following:

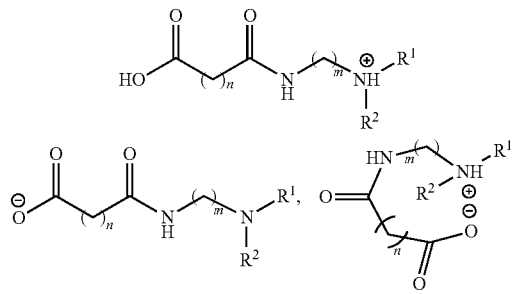

Therefore, the compound with a carboxyl acid group and an amide group disclosed by the invention has good water solubility and thus is applicable to a variety of fields, compared to the conventional solid salt materials.

DESCRIPTION OF THE PREFERRED EMBODIMENTS

Figure 1:
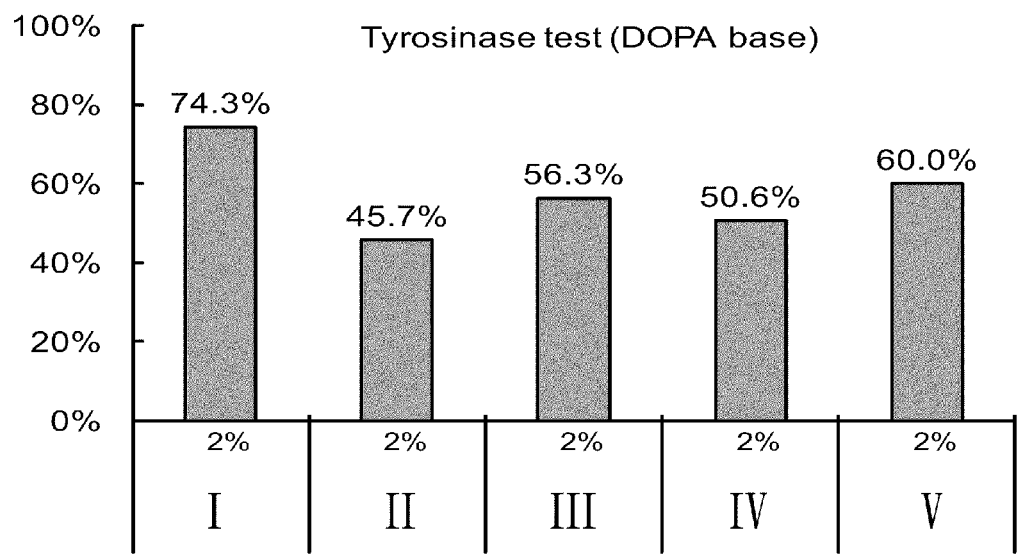
FIG. 1 shows a Mushroom Tyrosinase test (Dopa base) for the compound with a carboxyl acid group and an amide group of
(I) 8-(2-Dimethylamino-ethylcarbamoyl)-octanoic acid,
(II) 8-(2-Diisopropylamino-ethylcarbamoyl)-octanoic acid,
(III) 8-(3-Dimethylamino-propylcarbamoyl)-octanoic acid,
(IV) 9-(2-Dimethylamino-ethylcarbamoyl)-nonanoic acid, and
(V) 9-(3-Dimethylamino-propylcarbamoyl)-nonanoic acid.

What is probed into the invention is a compound with a carboxyl acid group and an amide group. Detail descriptions of the steps and compositions will be provided in the following in order to make the invention thoroughly understood. Obviously, the application of the invention is not confined to specific details familiar to those who are skilled in the art. On the other hand, the common compositions or steps that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In a first embodiment of the present invention, a compound with a carboxyl acid group and an amide group is disclosed.

The compound with a carboxyl acid group and an amide group has the following general equation:

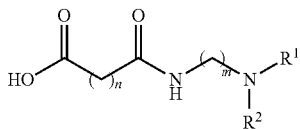

where n and m are both integers, n is 6~10, m is 2~4; $R^1$ and $R^2$ are the same, and $R^1$ and $R^2$ are C1~C6 alkyl groups. The C1~C6 alkyl groups comprise C1~C6 linear alkyl groups and C1~C6 branched alkyl groups. The above mentioned C1~C6 linear alkyl group comprises one group selected from the following: methyl, ethyl, n-propyl, n-butyl, n-pentyl, and n-hexyl. The above mentioned C1~C6 branched alkyl group comprises one group selected from the following: iso-propyl, iso-butyl, and iso-pentyl. The carboxyl acid group with a partial negative charge (δ−) and attracts the tertiary amino group to form a quaternary ammonium salt structure so that the compound is easy to dissolve in water. Two cases of the carboxyl acid group and the amide group attracting to each other are shown in the following:

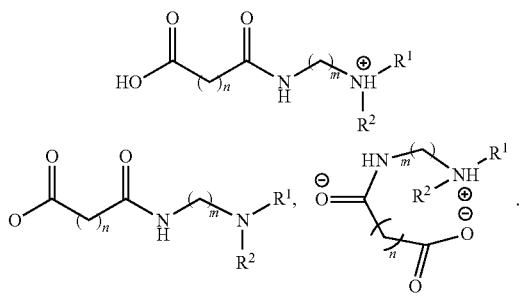

For the first case, the carboxyl acid group attracting the amino group at the tail of the amide group with each other occurs between two compounds while for the second case it occurs within one compound. The above mentioned compound is easy to dissolve in water and can be used to easily form an aqueous solution or oil-water mixture solution (w/o or o/w), such as emulsion or oil-water separated solution. Compared to other conventional solid salt compounds, the above mentioned compound does not require a dissolution procedure in advance and can be used directly but certainly can also undergo a dissolution procedure in advance.

The compound with a carboxyl acid group and an amide group can be independently selected from the group consisting of the following:

9-(3-dimethylamino-propylcarbamoyl) nonanoic acid having the following structure:

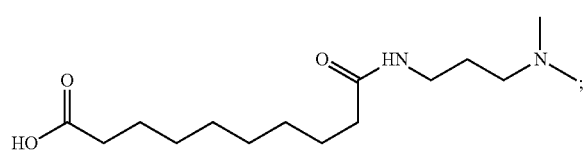

9-(2-dimethylamino-ethylcarbamoyl) nonanoic acid having the following structure:

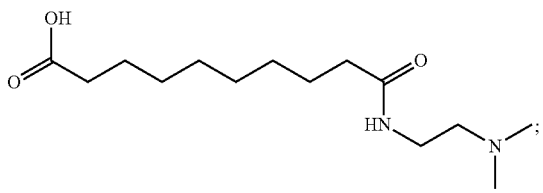

9-(2-diisopropylamino-ethylcarbamoyl) nonanoic acid having the following structure:

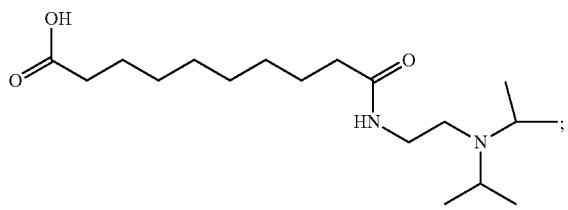

8-(3-dimethylamino-propylcarbamoyl)-octanoic acid having the following structure:

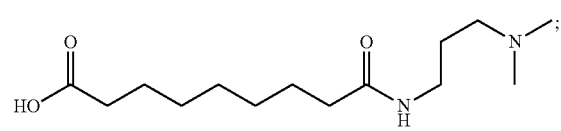

8-(2-dimethylamino-ethylcarbamoyl) octanoic acid having the following structure:

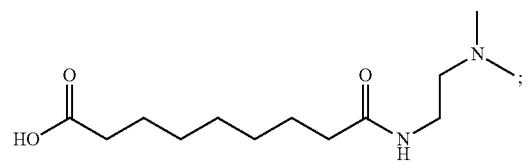

and
8-(2-diisopropylamino-ethylcarbamoyl) octanoic acid having the following structure:

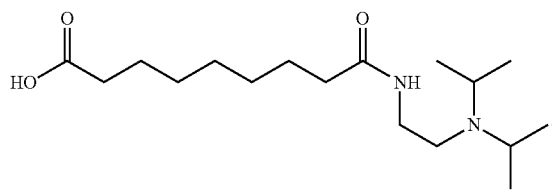

In a preferred example of this embodiment, the above mentioned compound with a carboxyl acid group and an amide group can be applied in cosmetics, skin care products, skin whitening products, sun-blocking products, cleansing products, as well as pharmaceutical and dermatological uses, etc.

In a second embodiment of the present invention, a compound with a carboxyl acid group and an amide group is disclosed. The above mentioned compound with a carboxyl acid group and an amide group is formed by a reaction of

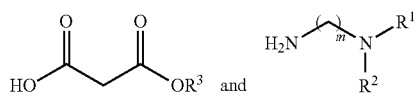

and having the following general equation:

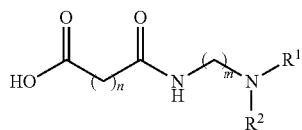

where n and m are both integers, n is 6~10, m is 2~4; $R^1$ and $R^2$ are the same, and $R^1$ and $R^2$ are C1~C6 alkyl groups. The C1~C6 alkyl groups comprise C1~C6 linear alkyl groups and C1~C6 branched alkyl groups. $R^3$ is a hydrogen atom or C1~C6 alkyl group. The carboxyl acid group has a partial negative charge (δ−) and attracts the tertiary amino group to form a quaternary ammonium salt structure so that the compound is easy to dissolve in water. The carboxyl acid group and the amide group attracting to each other is shown in the following:

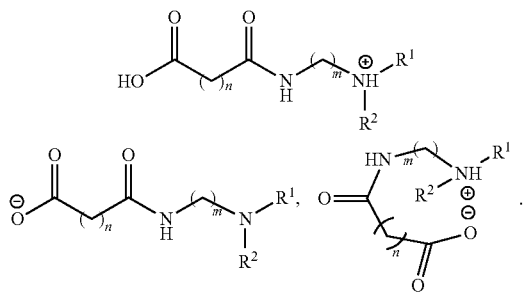

The above mentioned compound is easy to dissolve in water and can be used solely as one single raw material or blended with other raw materials. The above mentioned compound can be used to easily form an aqueous solution or oil-water mixture solution (w/o or o/w). Compared to other solid salt raw materials, the above mentioned compound does not require dissolving in solvent before use, that is, does not require a dissolution procedure which is required for a conventional salt raw material and thus simplifies the process. While the compound according to the invention is in use, it can be (1) directly added into the solution of raw materials or (2) dissolved to become a solution before blended with other raw materials.

In a preferred example of this embodiment, the above mentioned compound with a carboxyl acid group and an amide group can be applied in cosmetics, skin care products, whitening products, sun-blocking products, and cleansing products.

In another preferred example of this embodiment, the above mentioned compound with a carboxyl acid group and an amide group can be applied in pharmaceutical and dermatological uses, etc.

In a third embodiment of the present invention, a synthetic method for a compound with a carboxyl acid group and an amide group, having the following general equation:

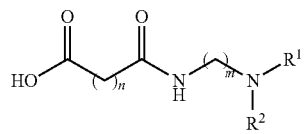

is disclosed.

A synthetic reaction to form the above mentioned compound with a carboxyl acid group and an amide group is shown in the following:

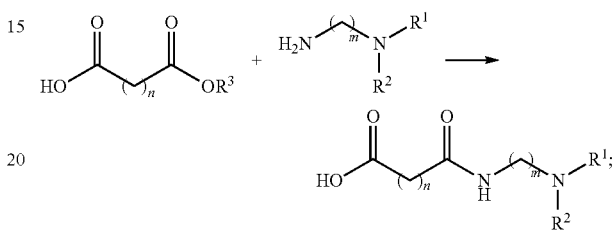

where the above reaction can further comprise a blending procedure and furthermore can comprise a heating procedure.

In the above, n and m are both integers, n is 6~10, m is 2~4; $R^1$ and $R^2$ are the same, and $R^1$ and $R^2$ are independently selected from the group consisting of the following: C1~C6 alkyl groups. The C1~C6 alkyl groups comprise C1~C6 linear alkyl groups and C1~C6 branched alkyl groups. $R^3$ is a hydrogen atom or C1~C6 alkyl group. The carboxyl acid group has a partial negative charge (δ−) and attracts the amino group at the tail of the amide group with each other to form a quaternary ammonium salt structure so that the compound is easy to dissolve in water.

In a fourth embodiment of the present invention, a cosmetic comprising a compound with a carboxyl acid group and an amide group is disclosed. The above mentioned compound with a carboxyl acid group and an amide group has the following general equation:

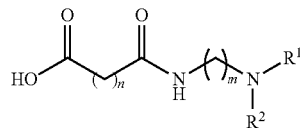

where n and m are both integers, n is 6~10, m is 2~4; $R^1$ and $R^2$ are the same, and $R^1$ and $R^2$ are C1~C6 alkyl groups. The C1~C6 alkyl groups comprise C1~C6 linear alkyl groups and C1~C6 branched alkyl groups. The carboxyl acid group has a partial negative charge (δ−) and attracts the amino group at the tail of the amide group with each other to form a quaternary ammonium salt structure so that the compound is easy to dissolve in water. The carboxyl acid group and the amide group attracting to each other is shown in the following:

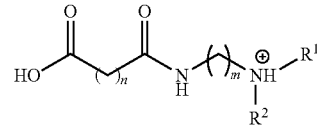

-continued

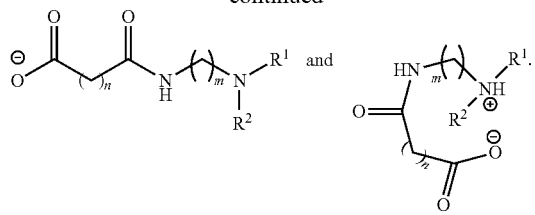

Compared to azelaic acid, the above mentioned compound is water soluble and is easier to dissolve in water. It can be used by way of an aqueous solution or oil-water mixture solution (w/o or o/w). Compared to other conventional solid salt cosmetic raw materials, the above mentioned compound can be used solely as one single raw material or blended with other raw materials. While the compound according to the invention is in use, it can be directly added into a mixture of liquid raw materials or can be dissolved in solvent and then blended with other raw materials. Either way can be used for the above mentioned compound.

The compound with a carboxyl acid group and an amide group can be independently selected from the group consisting of the following:

9-(3-dimethylamino-propylcarbamoyl) nonanoic acid having the following structure:

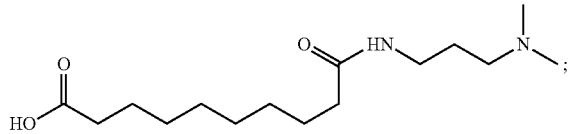

9-(2-dimethylamino-ethylcarbamoyl) nonanoic acid having the following structure:

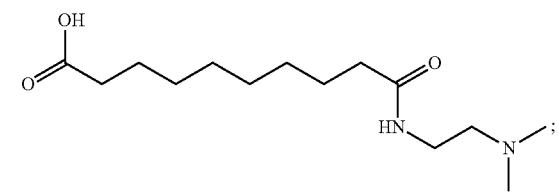

9-(2-diisopropylamino-ethylcarbamoyl) nonanoic acid having the following structure:

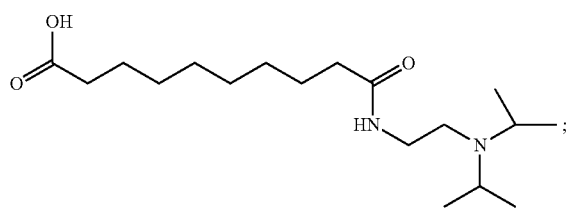

8-(3-dimethylamino-propylcarbamoyl)-octanoic acid having the following structure:

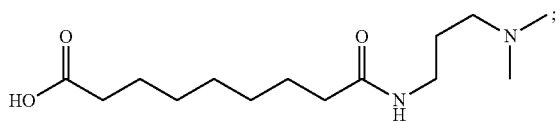

8-(2-dimethylamino-ethylcarbamoyl) octanoic acid having the following structure:

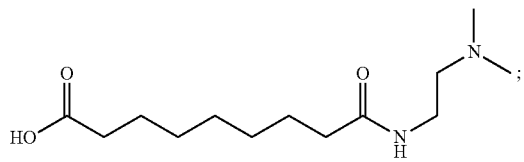

and 8-(2-diisopropylamino-ethylcarbamoyl) octanoic acid having the following structure:

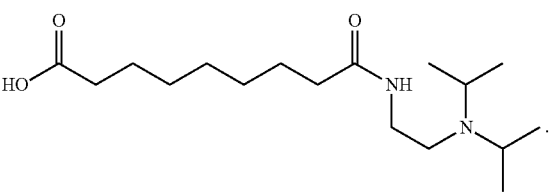

EXAMPLE

Synthesis of
8-(3-Dimethylamino-propylcarbamoyl)-octanoic acid

Azelaic acid (100 g, 0.532 mole) was dissolved in Methanol (100 mL) and then $H_2SO_4$ was added into reacted vessel. Reacted at reflux temperature for 3 hours. After reaction, Methanol was removed by evaporation. The crude mixture was extracted with Ethyl acetate/$H_2O$ and then evaporated to obtain di-methyl azelate. Di-methyl azelate (100 g, 0.462 mole) was dissolved in Methanol (100 mL), and then Ba(OH)$_2$.8H$_2$O (58.5 g, 0.185 mole) was poured into vessel. The mixture was reacted at 45° C. overnight. After reaction, Ba-salt was washed with Methanol and then acidified by HCl to get mono-methyl azelate.

Then, Mono-methyl azelate (10 g, 0.0495 mole) and N-Hydroxysuccinimide (6.26 g, 0.0544 mole) were dissolved in THF. A solution of Dicyclohexylcarbodiimide (12.24 g, 0.0592 mole) and THF was poured into the reacted vessel. Reacted at room temperature overnight, the DCU was removed by filter. Dimethylaminopropylamine (5.5 g, 0.0544 mole) was added into and reacted for overnight. Removed the solvent and extracted with Ethyl acetate/H₂O. After evaporation, 8-(3-Dimethylamino-propylcarbamoyl)-octanoic acid methyl ester was obtain. 8-(3-Dimethylamino-propylcarbamoyl)-octanoic acid methyl ester was dissolved in Methanol and added NaOH/Methanol (1 N, 50 ml). The mixture was stirred at room temperature for 3~6 hours and concentrated under vacuum. The residue was acidified with HCl/Ethyl acetate (1 N 55 ml). The crude was purified by column chromatography Ethyl acetate/Methanol to obtain [8-(3-Dimethylamino-propylcarbamoyl)-octanoic acid.hydrochloride].

Identification Analysis:

The basic data of 8-(2-Dimethylamino-ethylcarbamoyl)-octanoic acid (I) is shown as follows:

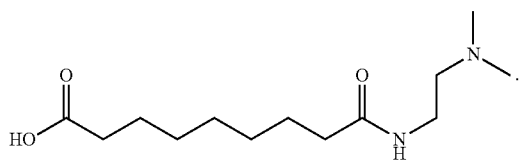

From the Mass-ESI spectrum, its molecular weight is 258. NMR 1H: 1.33, b, 6H, 1.58~1.61, b, 4H, 2.14~2.20, m, 4H, 2.62~2.65, t, 2H, 3.30~3.38, t, 2H, 4.94~4.95, b, 1H.

The basic data of 8-(2-Diisopropylamino-ethylcarbamoyl)-octanoic acid (II) is shown as follows:

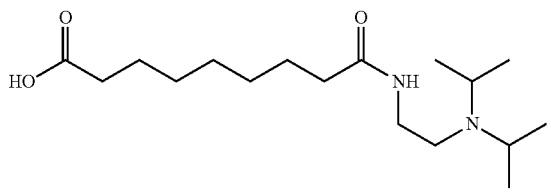

From the Mass-ESI spectrum, its molecular weight is 314. NMR 1H: 1.32, 1.33, 1.35, 3 s, 12H, 1.40~1.41, m, 6H, 1.60~1.61, b, 4H, 2.24~2.27, m, 4H, 3.20~3.26, m, 2H, 3.54~3.57, t, 2H, 3.78~3.80, m, 2H, 4.88, b, 1H.

The basic data of 8-(3-Dimethylamino-propylcarbamoyl)-octanoic acid (III) is shown as follows:

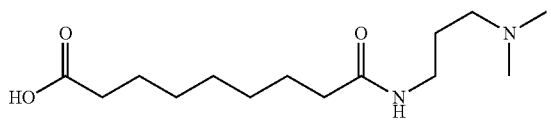

From the Mass-ESI spectrum, its molecular weight is 272. NMR 1H: 1.33, b, 6H, 1.57~1.63, m, 4H, 1.84~1.90, m, 2H, 2.14~2.21, m, 4H, 2.68, s, 6H, 2.90~2.93, s, t, 2H, 3.23~3.25, t, 2H, 5.15, s, 1H.

The basic data of 9-(2-Dimethylamino-ethylcarbamoyl)-nonanoic acid (IV) is shown as follows:

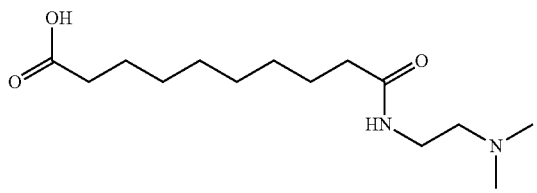

From the Mass-ESI spectrum, its molecular weight is 272. NMR: 1.3-1.4, s, 8H; 1.49-1.62, m, 4H; 2.0-2.24, m, 4H; 2.8, s, 6H; 3.1, t, 2H; 3.5, m, 2H; 4.8, s, 1H.

The basic data of 9-(3-Dimethylamino-propylcarbamoyl) nonanoic acid (V) is shown as follows:

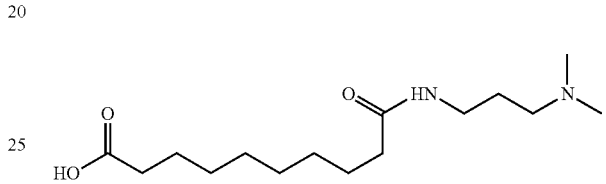

NMR: 1.2, s, 8H; 1.46-1.50, m, 4H; 1.7, m, 2H; 2.0, t, 2H; 2.1, t, 2H; 2.6, s, 6H; 2.8, t, 2H; 3.0, m, 2H; 7.9, s, 1H; 11.4, s, 1H.

The basic data of 9-(2-Diisopropylamino-ethylcarbamoyl)-nonanoic acid (VI) is shown as follows:

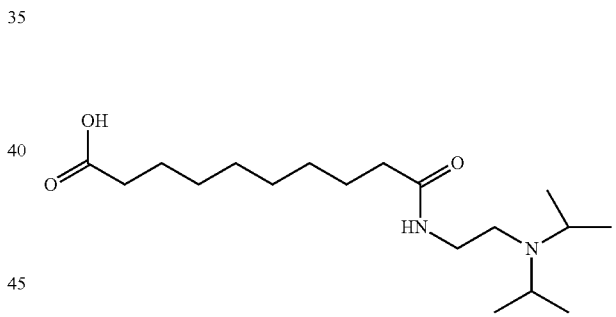

From the Mass-ESI spectrum, its molecular weight is 328.

Mushroom Tyrosinase Inhibition Test (Dopa Base):

Preparation: L-Dopa (L-3,4-dihydroxyphenylalanine; 1 mg/mL) was dissolved in pH 6.5 buffer solution. Samples were dissolved in water and prepared the concentration at 2%.

Method: 900 μL of L-Dopa solution was added into 100 μL of sample solution (or blank solution) and measured by thermo spectronic 475 nm ($A_{so}$ or $A_{b0}$). 15 μL of mushroom tyrosine buffer solution was added into mixture. After reaction for 3 min, mixture was measured by thermo spectronic ($A_{s3}$ or $A_{b3}$) (FIG. 1). Calculation:

$$\text{Inhibition \%} = 100 \times \frac{(A_{b3} - A_{b0}) - (A_{s3} - A_{s0})}{(A_{b3} - A_{b0})}$$

TABLE 1

Mushroom Tyrosinase Inhibition (Dopa base)

| Sample | Mushroom Tyrosinase Inhibition |
|---|---|
| (I)8-(2-Dimethylamino-ethylcarbamoyl)-octanoic acid | 74.3% |
| (II)8-(2-Diisopropylamino-ethylcarbamoyl)-octanoic acid | 45.7% |
| (III)8-(3-Dimethylamino-propylcarbamoyl)-octanoic acid | 56.3% |
| (IV)9-(2-Dimethylamino-ethylcarbamoyl)-nonanoic acid | 50.6% |
| (V)9-(3-Dimethylamino-propylcarbamoyl)-nonanoic acid | 60.0% |

Mushroom Tyrosinase Inhibition Test (Tyrosine Base):

Preparation: Tyrosine (5 mg/mL) were dissolved in pH 6.5 buffer solution. Samples were dissolved in water and prepared the concentration at 2%.

Figure 2:
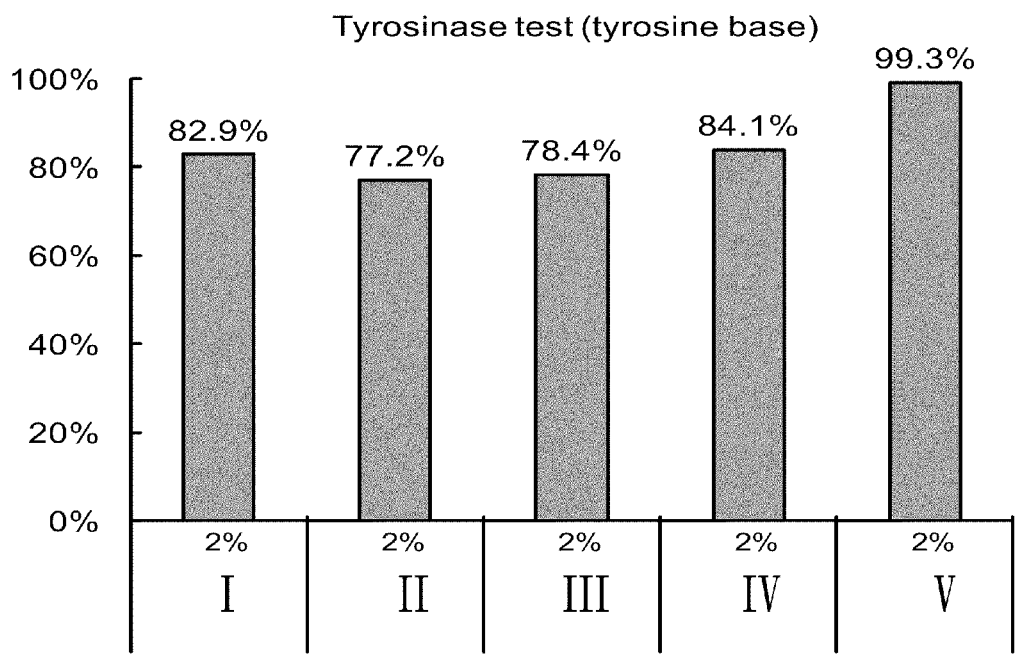
FIG. 2 shows a Mushroom Tyrosinase test (Tyrosine base) for the compound with a carboxyl acid group and an amide group of
(I) 8-(2-Dimethylamino-ethylcarbamoyl)-octanoic acid,
(II) 8-(2-Diisopropylamino-ethylcarbamoyl)-octanoic acid,
(III) 8-(3-Dimethylamino-propylcarbamoyl)-octanoic acid,
(IV) 9-(2-Dimethylamino-ethylcarbamoyl)-nonanoic acid, and
(V) 9-(3-Dimethylamino-propylcarbamoyl)-nonanoic acid.

Method: 900 μL of Tyrosine solution was added into 100 μL of sample solution (or blank solution) and measured by thermo spectronic 492 nm ($A_{so}$ or $A_{b0}$). 40 μL of mushroom tyrosinase buffer solution was added into mixture. After reaction for 60 minutes, the mixture was measured by thermo spectronic ($A_{s60}$ or $A_{b60}$) (FIG. 2). Calculation:

$$\text{Inhibition \%} = 100 \times \frac{(A_{b60} - A_{b0}) - (A_{s60} - A_{s0})}{(A_{b60} - A_{b0})}$$

TABLE 2

Mushroom Tyrosinase inhibition test (Tyrosine base)

| Sample | Mushroom Tyrosinase Inhibition |
|---|---|
| (I)8-(2-Dimethylamino-ethylcarbamoyl)-octanoic acid | 82.9% |
| (II)8-(2-Diisopropylamino-ethylcarbamoyl)-octanoic acid | 77.2% |
| (III)8-(3-Dimethylamino-propylcarbamoyl)-octanoic acid | 78.4% |
| (IV)9-(2-Dimethylamino-ethylcarbamoyl)-nonanoic acid | 84.1% |
| (V)9-(3-Dimethylamino-propylcarbamoyl)-nonanoic acid | 99.3% |

TABLE 3

Water Solubility

| Sample | Water Solubility |
|---|---|
| Azelaic acid | <0.5% |
| Sebacic acid | <0.1% |
| (II)8-(2-Diisopropylamino-ethylcarbamoyl)-octanoic acid | 22% |
| (III)8-(3-Dimethylamino-propylcarbamoyl)-octanoic acid | 33% |
| (IV)9-(2-Dimethylamino-ethylcarbamoyl)-nonanoic acid | 17% |
| (V)9-(3-Dimethylamino-propylcarbamoyl)-nonanoic acid | 29% |

Obviously many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. A compound with a carboxyl acid group and an amide group, having the following general equation:

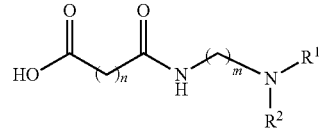

wherein n and m are both integers, n is 6~10, m is 2~4;

$R^1$ and $R^2$ are the same, $R^1$ and $R^2$ are C1~C6 alkyl groups where the C1~C6 alkyl groups comprise C1~C6 linear alkyl groups and C1~C6 branched alkyl groups;

the carboxyl acid group with a partial negative charge (δ−) attracts the tertiary amino group to form a quaternary ammonium salt structure so that the compound is easy to dissolve in water; and the carboxyl acid group and the amide group attracting to each other is shown in the following:

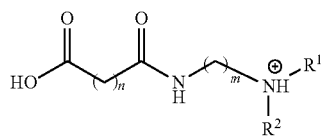

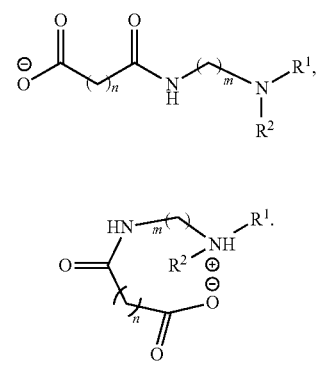

2. The compound according to claim 1, applicable to cosmetics, skin care products, whitening products, sun-blocking products, cleansing products, pharmaceutical and dermatological uses.

3. The compound according to claim 1, wherein the compound with a carboxyl acid group and an amide group is 9-(3-dimethylamino-propylcarbamoyl) nonanoic acid having the following structure:

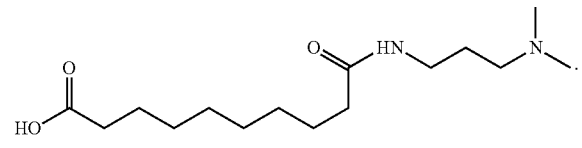

4. The compound according to claim 1, wherein the compound with a carboxyl acid group and an amide group is 9-(2-dimethylamino-ethylcarbamoyl) nonanoic acid having the following structure:

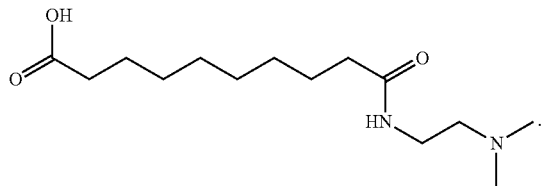

5. The compound according to claim 1, wherein the compound with a carboxyl acid group and an amide group is 9-(2-diisopropylamino-ethylcarbamoyl) nonanoic acid having the following structure:

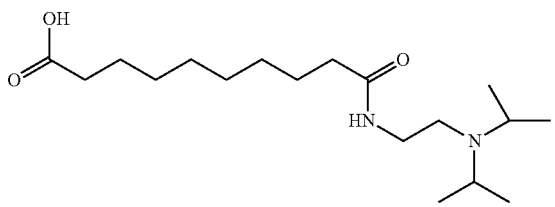

6. The compound according to claim 1, wherein the compound with a carboxyl acid group and an amide group is 8-(3-dimethylamino-propylcarbamoyl)-octanoic acid having the following structure:

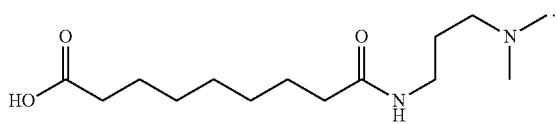

7. The compound according to claim 1, wherein the compound with a carboxyl acid group and an amide group is 8-(2-dimethylamino-ethylcarbamoyl) octanoic acid having the following structure:

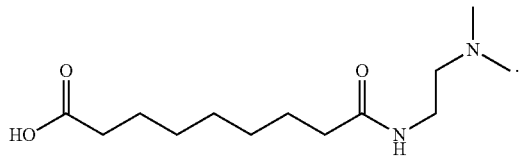

8. The compound according to claim 1, wherein the compound with a carboxyl acid group and an amide group is 8-(2-diisopropylamino-ethylcarbamoyl) octanoic acid having the following structure:

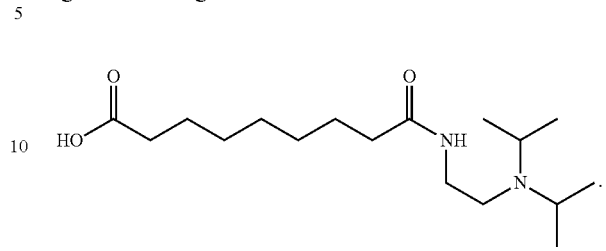

9. The compound according to claim 1, wherein the carboxyl acid group has a partial negative charge ($\delta-$) and attracts the amino group at the tail of the amide group with each other so that the solubility of the compound is more than or equal to 5%.

10. The compound according to claim 1, wherein the inhibition of the compound is more than 30% in a mushroom tyrosinase test (Dopa base).

11. The compound according to claim 1, wherein the inhibition of the compound is more than 60% in a mushroom tyrosinase test (tyrosine base).

12. A cosmetic, comprising a compound with a carboxyl acid group and an amide group having the following general equation:

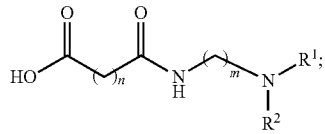

wherein n and m are both integers, n is 6~10, m is 2~4;

$R^1$ and $R^2$ are the same, $R^1$ and $R^2$ are C1~C6 alkyl groups;

the carboxyl acid group with a partial negative charge ($\delta-$) attracts the tertiary amino group to form a quaternary ammonium salt structure so that the compound is easy to dissolve in water.

13. The cosmetic according to claim 12, wherein the compound with a carboxyl acid group and an amide group is 9-(3-dimethylamino-propylcarbamoyl) nonanoic acid having the following structure:

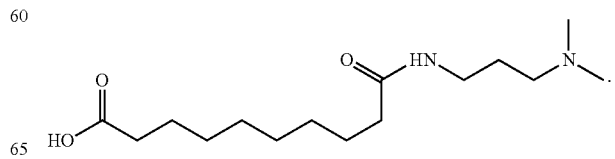

14. The cosmetic according to claim 12, wherein the compound with a carboxyl acid group and an amide group is 9-(2-dimethylamino-ethylcarbamoyl) nonanoic acid having the following structure:

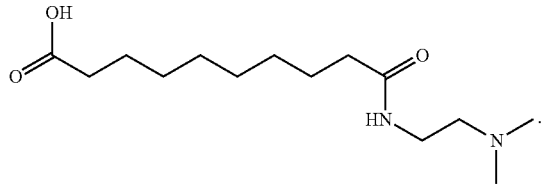

15. The cosmetic according to claim 12, wherein the compound with a carboxyl acid group and an amide group is 9-(2-diisopropylamino-ethylcarbamoyl) nonanoic acid having the following structure:

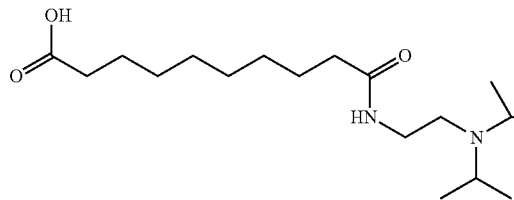

16. The cosmetic according to claim 12, wherein the compound with a carboxyl acid group and an amide group is 8-(3-dimethylamino-propylcarbamoyl)-octanoic acid having the following structure:

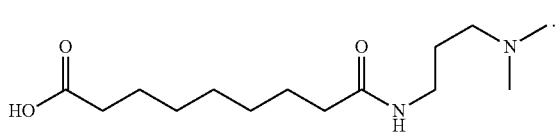

17. The cosmetic according to claim 12, wherein the compound with a carboxyl acid group and an amide group is 8-(2-dimethylamino-ethylcarbamoyl) octanoic acid having the following structure:

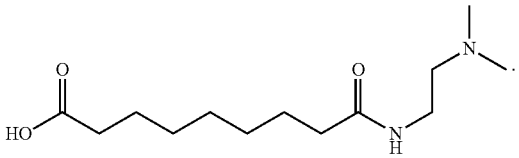

18. The cosmetic according to claim 12, wherein the compound with a carboxyl acid group and an amide group is 8-(2-diisopropylamino-ethylcarbamoyl) octanoic acid having the following structure:

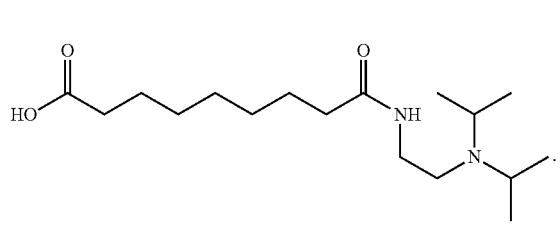

19. The cosmetic according to claim 12, wherein the carboxyl acid group has a partial negative charge ($\delta-$) and attracts the amino group at the tail of the amide group with each other so that the solubility of the compound is more than or equal to 5%.

* * * * *